United States Patent [19]
Lynn et al.

[11] Patent Number: 5,147,398
[45] Date of Patent: Sep. 15, 1992

[54] MULTIPLE COMPARTMENT BREAST PROSTHESIS

[76] Inventors: Lawrence A. Lynn, 1275 Olentangy River Rd., Suite 202, Columbus, Ohio 43212; Mark Foglietti, 3755 Orange Pl., Cleveland, Ohio 44122

[21] Appl. No.: 721,262

[22] Filed: Jun. 26, 1991

Related U.S. Application Data

[62] Division of Ser. No. 518,709, May 4, 1990, Pat. No. 5,092,882.

[51] Int. Cl.⁵ ............................................... A61F 2/12
[52] U.S. Cl. ...................................................... 623/8
[58] Field of Search ...................................... 623/7, 8

[56] References Cited

U.S. PATENT DOCUMENTS

| | | | |
|---|---|---|---|
| 4,298,998 | 11/1981 | Naficy | 623/8 |
| 4,605,412 | 8/1986 | LaForest et al. | 623/8 |
| 4,648,880 | 3/1987 | Brauman | 623/8 |
| 4,650,487 | 3/1987 | Chaglassian | 623/8 |
| 4,733,909 | 9/1988 | Chaglassian | 623/8 |
| 4,790,848 | 12/1988 | Cronin | 623/8 |
| 4,820,303 | 4/1989 | Brauman | 623/8 |

FOREIGN PATENT DOCUMENTS 2199266  4/1974  France ................................. 623/8

*Primary Examiner*—Ronald Frinks
*Attorney, Agent, or Firm*—Longacre & White

[57] ABSTRACT

An improved breast prosthesis for insertion under the sub-cutaneous tissue or muscle of the chest wall formed as a plurality of compartments each containing silicone gel or the like. The surface area to volume ratio of the apical compartment is smaller than the basilar one so that the appearance of projection is produced and pressure on the apex results in basilar deformation, reducing the perception of apical firmness. Preferably the skin is of PTFE possibly reducing capsular contractive and the perception of excessive firmness.

4 Claims, 1 Drawing Sheet

MULTIPLE COMPARTMENT BREAST PROSTHESIS

CROSS-REFERENCE TO RELATED APPLICATIONS

This application is a division of application Ser. No. 518,709 filed May 4, 1990, now U.S. Pat. No. 5,092,882.

BACKGROUND AND SUMMARY OF THE INVENTION

The invention relates to augmentation mammoplasty and reconstructive breast surgery and to an improved breast prostheses.

Conventional breast prostheses generally are constructed as a single unit containing gelatinous material such as silicone gel surrounded by a single envelope typically made of silicone. These prostheses are placed under the subcutaneous tissue of the breast or under the pectoralis muscle. The effect of the prosthesis is to enlarge the base of the breast. However, in many cases, and in particular after breast resection, enough subcutaneous tissue may not be present to provide adequate projection of the breast. The insertion of a larger prosthesis simply results in a pancaking effect since the prosthesis is soft to provide the normal feel of breast tissue and therefore tends to flatten. Increasing the viscosity of the gel within the breast can result in less flattening of the prothesis. However, this also results in an abnormal sense of firmness of the breast. To compensate, a technique of stacking one prosthesis on top of another during surgical implantation of the breast has been proposed. However, such a technique can result in a flattening of both prostheses and is technically more difficult than the insertion of a single prosthesis.

A second problem relates to the formation of capsular contractures associated with tissue reaction to the implanted prosthesis. This problem is well known in the art and causes an abnormal sense of firmness of the enhanced breasts in a substantial percentage of patients.

In general, the improved breast prosthesis of the present invention is formed as a conical or pyramidal implant having a base which has a larger surface area than the apex which is preferably rounded. In the preferred embodiment the prosthesis includes a plurality of compartments which are surrounded by a single envelope or housing means. The base compartment has a larger surface area to volume ratio and therefore is more easily deformable than the more apical compartments. In other words, the walls of the basilar compartment which are adapted to be positioned relatively proximally are stretched less than the walls of the apical compartment which are adapted to be positioned relatively distally and therefore the internal pressure is less as well.

In the preferred embodiment three compartments are provided, each with a progressively decreasing exterior surface area to volume ratio from the base to the apex. The compartments may be attached one to another as by adhesive and covered by a single envelope or they may be preferably integral, one with another, comprising individual compartments of a single pyramidal structure.

Each compartment is preferably filled with suitable permanently deformable material such as conventional silicone. The surrounding envelope is preferably porous polytetrafluoroethylene, (PTFE) which can be obtained under the trade name GORTEX. The assembled prosthesis, when placed upon it's base, will assume a substantially conical shape having a rounded apex. The apical compartment will have a slighter firmer feel to palpation than the basilar compartment.

In operation the prosthesis is placed under the breast tissue or pectoralis muscle with the apex facing outwardly or distally. The feel of the prosthetically enhanced breast will be substantially natural in that, while the apex of the breast is firmer than the base, pressure upon the apex results in basilar deformation thereby reducing the perception of apical firmness. However, the firmness of the apical portion produces the appearance of projection which is considered more aesthetically appealing to the patient. The porous polytetrafluoroethylene envelope or housing means provides a novel interface between the breast implant and the patient's surrounding tissue. This may potentially reduce capsular contracture and therefore reduce the perception of excessive firmness which may develop with conventional implants.

DESCRIPTION OF THE PREFERRED EMBODIMENT

Figure 1:
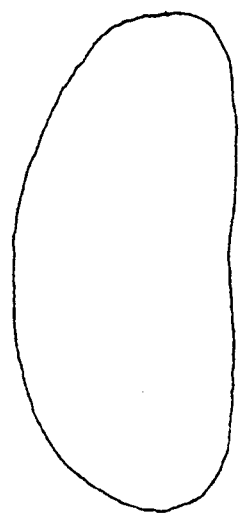
FIG. 1 is a side view of a conventional breast implant.

The invention comprises, in general, an improved breast prosthesis 10 with a roughly conical or pyramidal shape having a rounded apex 12. More particularly, the prosthesis 10 resembles and responds to pressure like a natural breast. The tendency to flatten like a pancake which is inherent in a conventional prosthesis 11 as shown in FIG. 1 is avoided.

Figure 3:
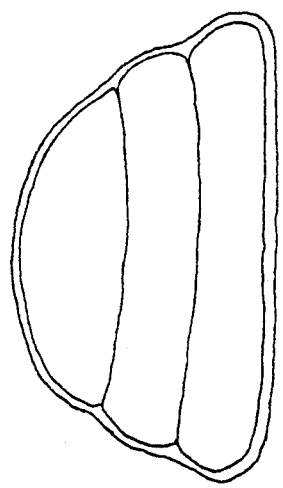
FIG. 3 is a sectional view through the apex of the preferred embodiment showing the three separate compartments.
Figure 2:
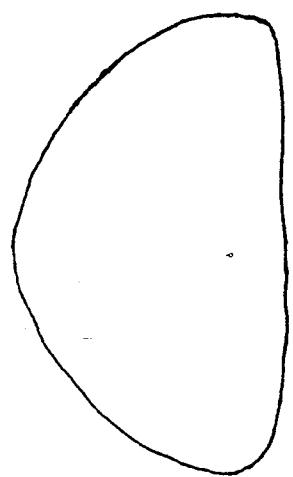
FIG. 2 is the side view of the preferred embodiment of the present invention.

FIGS. 2 and 3 demonstrates the preferred embodiment in which this object is achieved by providing three separate compartments or chambers 14, 16, and 18 having respective interior walls 20, 22, and 24 which are integral one with another. Each compartment is filled with conventional silicone or other gel 26. The walls 20, 22, and 24 of the compartments 14, 16, and 18 are formed of silicone or other suitable material, as is known in the art. The compartments are isolated one from the other so that the contents thereof cannot readily migrate from compartment to compartment.

The basilar chamber 18 has a larger internal wall surface area to internal volume ratio than the middle chamber 16 and the middle chamber 16 has a larger internal wall surface area to internal volume ratio than the apical chamber 14. Thus, a greater sense of firmness in the apical chamber 14 is provided than in the basilar chamber 18 since the pressure at rest within the basilar chamber is less than in the apical chamber. In addition, this provides for apical projection when the prosthesis 10 is placed on the basilar compartment 18.

An outer surrounding housing means or envelope 30, preferably of porous polytetrafluoroethylene (PTFE), is provided to reduce tissue reaction to the prosthesis 10 and therefore reduce capsular contracture due to reaction of the patient's body tissue to the prosthesis. The volume of the outer housing means or envelope 30 is substantially equal to the combined volumes of the apical and basilar compartments.

Other approaches can be taken to providing that the multi-compartment prosthesis responds to pressure like a natural breast. The pressure in the respective compartments of the gel can be made deliberately different resulting in greater stretching in the apical compartment and a greater firmness. The firmness of the gel can likewise be deliberately made greater in the apical compartment by using gel having a greater viscosity.

Many other changes and modifications in the above described embodiments of the invention can of course be made without departing from the scope thereof. For example while three compartments are preferable, more can be provided if desired and the invention provides good results with only a basilar and apilar compartment. Accordingly, that scope is intended to be limited only by the scope of the appended claims.

We claim:

1. A breast prosthesis for insertion under subcutaneous tissue of a chest wall, the prosthesis comprising:
    an apical compartment having a relatively low surface area to volume ratio and adapted to be positioned relatively distally;
    a basilar compartment having a relatively high surface area to volume ratio and adapted to be positioned relatively proximally;
    said apical compartment and said basilar compartment are each filled with a single permanently deformable material and said apical and basilar compartments are mutually exclusive to one another; and
    outer housing means for positionally fixing said apical and basilar compartments with respect to one another and adapted to envelope said apical and basilar compartments, wherein the volume of said outer housing means is substantially equal to the combined volumes of said apical and said basilar compartments.

2. The breast prosthesis of claim 1, wherein said apical and basilar compartments share a common wall.

3. The breast prosthesis of claim 1, wherein said basilar compartment has a relatively larger volume with respect to said apical compartment.

4. The breast prosthesis of claim 1, wherein said outer housng means is porus polytetrafluoroethylene.

* * * * *